United States Patent [19]

Petrovich

[11] 4,452,781
[45] Jun. 5, 1984

[54] METHOD OF TREATING BACTERIAL VIRAL OR PARASITIC DISEASES

[76] Inventor: Vojislav Petrovich, 1935 W. Schiller St., Chicago, Ill. 60622

[21] Appl. No.: 431,783

[22] Filed: Sep. 30, 1982

Related U.S. Application Data

[63] Continuation-in-part of Ser. No. 187,584, Sep. 15, 1980, abandoned, Ser. No. 187,585, Sep. 15, 1980, abandoned, Ser. No. 196,882, Oct. 14, 1980, abandoned, Ser. No. 233,036, Feb. 9, 1981, abandoned, Ser. No. 233,037, Feb. 9, 1981, abandoned, Ser. No. 287,428, Jul. 27, 1981, abandoned, Ser. No. 288,302, Jul. 30, 1981, abandoned, Ser. No. 288,304, Jul. 30, 1981, abandoned, Ser. No. 294,849, Mar. 21, 1981, abandoned, Ser. No. 294,850, Aug. 21, 1981, abandoned, Ser. No. 298,178, Aug. 31, 1981, abandoned, Ser. No. 400,590, Jul. 22, 1982, abandoned, Ser. No. 400,591, Jul. 22, 1982, abandoned, and Ser. No. 400,592, Jul. 22, 1982, abandoned.

[51] Int. Cl.$^3$ .................... A61K 33/04; A61K 31/19; A61K 31/205
[52] U.S. Cl. .................................. 424/164; 424/317; 424/319
[58] Field of Search ........................ 424/164, 319, 317

[56] References Cited

U.S. PATENT DOCUMENTS

| | | | |
|---|---|---|---|
| 2,917,429 | 12/1959 | Scott | 424/336 |
| 3,167,471 | 1/1965 | Kovacs | 424/164 |
| 3,846,459 | 11/1974 | Stapfer | 260/429.7 |
| 3,976,781 | 8/1976 | Kalopissis | 424/309 |
| 4,107,330 | 8/1978 | Sheffner | 424/317 |
| 4,148,885 | 4/1979 | Renoux | 424/317 |
| 4,151,301 | 4/1979 | Kalopissis | 424/316 |
| 4,378,349 | 3/1983 | Petrovich | 424/164 |
| 4,378,350 | 3/1983 | Petrovich | 424/164 |
| 4,378,351 | 3/1983 | Petrovich | 424/164 |

FOREIGN PATENT DOCUMENTS 2917790  11/1979  Fed. Rep. of Germany .

Primary Examiner—Jerome D. Goldberg
Assistant Examiner—John W. Rollins

[57] ABSTRACT

The invention relates to a therapeutic mixture for treating bacterial and viral infections and exterminating parasites in human and animal host; comprises a therapeutically effective mixture consisting of homocysteine sodium salt, which is aminomercaptobutyric acid and dipotassium hydrosulfate, which in conjunction perform after injection a permanent reducing action liberating charged hydrogen, and charged aminothiobutyric acid radical, which are biologically active neutralizing and transforming bacteria and viruses, and kill the parasites.

3 Claims, No Drawings

METHOD OF TREATING BACTERIAL VIRAL OR PARASITIC DISEASES

This application is a continuation in part of the applications: Ser. No. 187,584, filed Sept. 15, 1980, Ser. No. 187,585, filed Sept. 15, 1980, Ser. No. 196,882, filed Oct. 14, 1980, Ser. No. 233,036, filed Feb. 9, 1981, Ser. No. 233,037, filed Feb. 9, 1981, Ser. No. 287,428, filed July 27, 1981, Ser. No. 288,302, filed July 30, 1981, Ser. No. 288,304, filed July 30, 1981, Ser. No. 294,849 filed Mar. 21, 1981, Ser. No. 294,850, filed Aug. 21, 1981, Ser. No. 298,178, filed Aug. 31, 1981, Ser. No. 400,590, filed July 22, 1982, Ser. No. 400,591, filed July 22, 1982, Ser. No. 400,592, filed July 22, 1982, which are all abandoned.

This invention relates to a therapeutic action of reducing media for controlling bacterial and viral infection and parasitic infestion in human and animal host, by applying a therapeutic mixture consisting of aminomercaptobutyric acid sodium salt and dipotassium hydrosulfate. Said aminomercaptobutyric sodium salt in conjunction with reducing dipotassium hydrosulfate perform after injection a permanent reducing action liberating charged hydrogen, and charged aminothiobutyric radical which are biologically active, which is manifested by neutralizing, or transforming the bacteria and viruses to nonaggressive macromolecules, while killing parasites.

The mechanism of action of aminomercaptobutyric sodium salt in conjunction with dipotassium hydrosulfate unfolds a reducing process in a reducing media, which consequently contributes to the development of nascent and biologically active charged hydrogen, as well as the development of nascent charged aminothiobutyric acid radical. The supposedly antibacterial and antiviral action is accomplished by the integration of charged hydrogen and charged aminothiobutyric acid radical derived from reduced aminomercaptbutyric sodium salt, which complete the bacterial and viral nucleoproteides and thus neutralize their activity, while charged aminothiobutyric radical which being unstable when unite to bis-(aminobutyric)disulfide in the presence of parasites, said bis-(aminobutyric)disulfide is poisonous to parasites and thus kills them.

The regenerative reversible process in the formation of aminomercaptobutyric sodium salt and aminothiobutyric radical to release the active charged hydrogen develops by inherent oxidizing process and the reducing action of dipotassium hydrosulfate. The reverse process is manifested in permanently reducing charged aminothiobutyric radical to aminomercaptobutyric acid as long as it is of disposable hydrogen from hydrosulfate reducing action developed by hydrolysis. Each oxidation and reduction is sustained in reversible conditions, which is very important timely and biologically.

Reversible oxidation and reduction of aminomercaptobutyric acid makes feasible that the combination of said compound with mild reducing agent such as dipotassium hydrosulfate partake in the formation of biologically active hydrogen, i.e., charged hydrogen and charged aminothiobutyric radical. Combining charged hydrogen and charged aminothiobutyric radical follows de-oxidation and neutralization of bacteria and virus unsaturated macromolecules, while the parasites under such conditions are killed. Thus the nascent charged hydrogen, and nascent charged aminothiobutyric radical by their reactivity promote the killing of parasites, which is the essence of this invention.

The charged hydrogen and the charged aminothiobutyric radical are capable to bind unsaturated compounds on which behavior is based antibacterial and antiviral action of this invention. For, macromolecules undoubtedly have no homogeneous charge distribution, which should provide potential sites for trapping displaced electrons or binding holes in addition to those associated with lattice imperfection.

The advantage of disclosed pharmacologically active reducing media with charged hydrogen radical, charged aminothiobutyric radical, reside in non-toxic quality of disclosed process. No side effects can be expected by application of simple aminomercaptobutyric sodium salt, aided by dipotassium hydrosulfate with reducing capabilities by evolving disposable charged hydrogen. The aminothiobutyric radical is of short duration, because emitting charged hydrogen. Therefore, no toxic action may be incurred anyhow. The aminothiobutyric radical being unstable in neutral and weakly alkaline media as is the blood serum oxidizes to dislfide diacid by emitting hydrogen. The presence of dipotassium hydrosulfate prevents the formation of disulfide, as well as the presence of parasites, which is always present in said process but is of short duration. The dipotassium hydrosulfate oxidizes to dipotassium sulfate by the way of hydrolysis emitting two charged hydrogen. Because the presence of oxidation-reduction evolved in blood serum the presence of dipotassium hydrosulfate diminishes the needed presence of aminomercaptobutyric sodium salt for several times as pharmacologically needed to produce and emit charged hydrogen for biologic synthesis, whereas the charged aminothiobutyric radical is permanently and succeedingly incorporated in nucleoproteides of bacteria and viruses and/or in killing parasites until complete exhaustion and consummation. Thus, no toxic action can be incurred, while dipotassium sulfate the only unassimilable product is eliminated from the organism.

Explaining the possible mechanism of action in controlling bacteria, viruses, and parasites it was observed that all purulent processes of chronic character, supurations, pustules, furuncles, various abcesses, various eczemas, purulent staphococial infections, streptococcal and other bacterial infections, mastitys, actinomycosis, actinobacillosis, mycosis, mycetes, endometritis may be healed with therapeutical mixture of this invention. Furthermore, myxovirus infection, mixomatosis and the like infections are successfully controlled. Of the parasitic diseases, the protozoan diseases, parasites of the type ixodides, Teliasis, the parasitic sickness of eye conjunctives in bovine, mange in bovine and all animals are successfully exterminated with therapeutical mixture of this invention.

The application in human is fulfilled with one injection at intervals of one or two days. The applications are fulfilled by priority intravenous, but may be applied also intramuscular. If applied intramuscular then the application is made in two places, i.e., in the left and the right thigh. When applied intramuscular certain irritation may be felt, otherwise no other consequences may appear. The doses may be increased until 12 injections in the course of healing. All is worked slowly. The intervals may be longer, which depends on the case. In cases of internal purulent processes and inflamations with suppurations and internal pustule the application must be gradual because the inneral pustule may close and form a scar, which may require an operation.

The standard combination of healing ingredients for human use is 200 mg of dry aminomercaptobutyric sodium salt, and 800 mg of dry dipotassium hydrosulfate, both dissolved before injection in 10 ccm distilled water per 24 hour period.

The standard combination of healing ingredients for animal use is stronger for big animals and the amount varies depending of the net weight of animal. Thus, for each 50 kg net weight of animal 1 ccm of 100 mg of dry aminomercaptobutyric sodium salt, and 300 mg of dry dipotassium hydrosulfate, both dissolved before injection in 1 ccm distilled water per 24 hour period.

What is claimed is:

1. A method for treating a human or animal host infected with bacteria and viruses or infested with parasites which comprises: administering to said host a pharmaceutical composition comprising, aminomercaptobutyric acid or its sodium salt and dipotassium hydrosulfate in amount effective to give a reducing action in vivo after injection, liberating charged hydrogen and charged aminithiobutyric radical for neutralizing bacteria and viruses and killing parasites.

2. The method of claim 1, where the pharmaceutical composition comprises 100 to 200 mg of dry aminomercaptobutyric acid or its sodium salt and 300 to 800 mg of dry dipotassium hydrosulfate dissolved in 1 to 10 ccm distilled water, which is injected intravenously or intramuscularly in the host in need of such treatment per 24 hour period.

3. The method of claim 1, for treating said human or animal host infected with bacteria or viruses, or infested with parasites which further comprises:

(a) treating said human or animal host in need of said treatment with repeated administration by intravenous injection or intramuscular injection in two sites with an antibacterial, antiviral and antiparasite effective amount therefore of a pharmaceutical mixture containing as active ingredients aminomercaptobutyric sodium salt and dipotassium sulfate;

(b) the dosage range per 24 hour period of the mixture in adult human patient being about 200 mg of dry aminomercaptobutyric sodium salt, and 800 mg of dry dipotassium hydrosulfate, both dissolved before injection in 10 ccm distilled water; and (c) the dosage range per 24 hour period of the mixture for grown animal being about 1 ccm for each 50 kg net weight of the animal, which mixture contains 100 mg of dry aminomercaptobutyric sodium salt, and 300 mg of dry dipotassium hydrosulfate, both dissolved before injection in 1 ccm distilled water.

* * * * *